(12) United States Patent
Ben Ayed

(10) Patent No.: US 7,565,132 B2
(45) Date of Patent: Jul. 21, 2009

(54) PORTABLE HEALTH MONITORING SYSTEM

(76) Inventor: Mourad Ben Ayed, 315 Charger St. #67, Revere, MA (US) 02151

( * ) Notice: Subject to any disclaimer, the term of this patent is extended or adjusted under 35 U.S.C. 154(b) by 626 days.

(21) Appl. No.: 11/204,482

(22) Filed: Aug. 17, 2005

(65) Prior Publication Data

US 2007/0042713 A1 Feb. 22, 2007

(51) Int. Cl.
*H04M 11/04* (2006.01)
(52) U.S. Cl. .............. 455/404.1; 455/404.2; 455/414.1; 455/414.3; 455/418; 455/420; 455/456.1; 455/456.2; 455/456.3; 455/457; 455/458; 455/41.2; 455/11.1; 455/556.1; 340/539.1; 340/539.11; 340/539.12; 340/539.22; 340/539.26; 340/539.27; 340/539.28; 340/825.36

(58) Field of Classification Search ... 455/404.1–404.2, 455/414.1–414.4, 415–416, 418–420, 456.1–456.6, 455/457–458, 41.1–41.2, 11.1, 556.1–556.2, 455/557, 564; 340/539.11, 573.1, 539.12, 340/539.13, 572.1, 825.49, 825.69, 573.4, 340/539.1, 539.22, 539.24, 539.26–539.28, 340/825.36
See application file for complete search history.

(56) References Cited

U.S. PATENT DOCUMENTS

| | | | |
|---|---|---|---|
| 6,992,580 B2 * | 1/2006 | Kotzin et al. | 340/539.11 |
| 7,221,928 B2 * | 5/2007 | Laird et al. | 455/404.1 |
| 2004/0199056 A1 * | 10/2004 | Husemann et al. | 600/300 |
| 2005/0153680 A1 * | 7/2005 | Yoshioka et al. | 455/404.1 |

* cited by examiner

*Primary Examiner*—Tuan A Tran
(74) *Attorney, Agent, or Firm*—Daniel B. Schein, Esq.

(57) ABSTRACT

A health monitoring system containing a Bluetooth transceiver and one or more health signs sensors automatically detects conditions that require medical attention based on configurable rules, calls a phone number and sends an alert.

14 Claims, 5 Drawing Sheets

PORTABLE HEALTH MONITORING SYSTEM

FIELD OF THE INVENTION

This invention is directed generally to health monitoring systems and more specifically to a portable device that monitors health signs and that automatically calls a phone number or sends an email when it detects a condition that requires medical attention.

BACKGROUND OF THE INVENTION

Existing health monitoring systems comprise a trigger device and a base station connected to a telephone jack that automatically dials an emergency service when a person activates the trigger device. These devices are costly and require a fixed phone line. These devices do not call automatically on detection of a condition that requires attention.

Another health monitoring systems is a pulse oximeter sensor that communicates with a base station using Bluetooth. The base station is capable of detecting a health condition and calling a number. This system is cumbersome and not easily portable as it is composed of two parts.

There is a need for a more convenient, portable and reliable method and apparatus for sending an alert when a condition that requires medical attention is detected.

SUMMARY OF INVENTION

A unitary remotely configurable portable health monitoring system comprising:
health sensor means for collecting data,
Bluetooth transceiver means for establishing a two-way wireless connection with a second device in range, memory for storing one or more alert messages,
one or more batteries,
a processor for evaluating data from health sensor means and comparing it to acceptable ranges,
if said data is outside said acceptable ranges, transmitting said alert messages when a first Bluetooth wireless connection has been established between said Bluetooth transceiver and a second device in range and a second cellular network connection has been established between said second device and a third communication device.

A method for health monitoring using a unitary remotely configurable rule-based portable monitoring system comprising:
periodically:
reading data from health sensor means,
comparing said data to acceptable thresholds,
on detecting an exception,
a transceiver is turned on,
a short range two-way wireless connection is established with a second wireless communication device in range compatible with said transceiver,
said second wireless communication device:
dials one or more alert phone numbers,
establishes cellular network communication with a third communication device and transmits one or more alert messages.

A method for health monitoring using a unitary remotely configurable rule-based portable monitoring system comprising:
reading data from health sensor means,
comparing said data to acceptable thresholds,
on detecting an exception,
a transceiver is turned on,
a short range two-way wireless connection is established with a second wireless communication device in range compatible with said transceiver, data from health sensor means is sent to said second wireless communication device,
said second wireless communication device:
dials one or more alert phone numbers,
establishes cellular network communication with a third communication device,
sends one or more alert messages.

BRIEF DESCRIPTION OF THE DRAWINGS

The present invention with be more clearly understood after reference to the following detailed specifications read in conjunction with the drawings wherein.

DETAILED DESCRIPTION OF THE PREFERRED EMBODIMENTS

Figure 1:
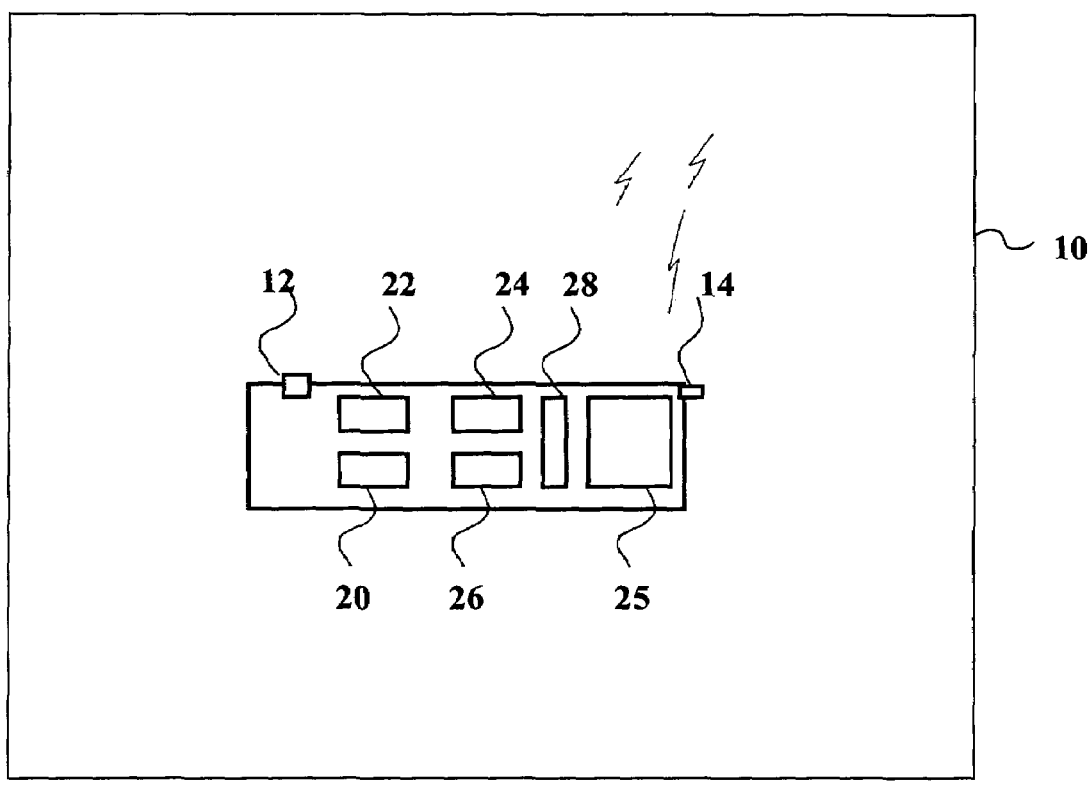
FIG. 1 is a schematic of a portable health monitoring system

FIG. 1 is schematic of a portable health monitoring system 10 comprising a processor 20 interconnected with switches 12, health sensors 22, memory 28, transceiver 26, battery 24, alert center 25 and antenna 14. An attachment system, such as a clip, ring, fastening mechanism may be attached to the portable health monitoring system.

Switches 12 can be any type of button, switch, remote sensor, touch sensor, contact sensor or activation system. Switches 12 are used to initiate or to reset the portable health monitoring system. Switches 12 may be used to turn on/off the portable health monitoring system or to shut off alert center 25.

Health sensors 22 can be simple arrangements to collect health data such as an infrared detector, a temperature reader, a blood pressure reader, a heart rate reader, an insulin reader, a prosthesis data reader, a vibration detector, a colour detector, a pulse oximeter, a $CO_2$ detector, aaccelerometers, gyros. Health sensors generate output signals that are indicative of sensed conditions. The output signals are converted to data sequences.

Transceiver 26 is any type of transceiver or a combination of transmitter and receiver. In a preferred embodiment, transceiver 26 conforms to BlueTooth specifications, 802.11, WiLAN, or any other communication protocol (BlueTooth may also be spelled Bluetooth, with both terms considered equivalent herein). Transceiver 26 can discover other compatible transceivers in the vicinity. Transceiver 26 can establish a temporary two-way connection or a piconet network with other devices equipped with compatible transceivers.

Battery 24 provides power to some of the components of portable health monitoring system 10. It will be understood that battery 24 may be a fuel cell, nickel-cadmium, lithium, alkaline or nickel-hydride battery or any other portable source of electric power. Battery 24 can also be replaced with photovoltaic cells.

When portable health monitoring system 10 is not in operation it remains in a dormant state ("sleep-mode") to conserve the energy of battery 24.

Alert center 25 can be any type of visual, audio, tactile or mechanical user interface means capable of conveying information to the user. An example of visual means is an LED, or any visual information display device. Audio means can be any audio device such as a speaker, a buzzer, a Piezo buzzer. Tactile means can be any tactile sensor such as a heat-generating device. An example of a mechanical means is a vibrator.

Antenna 14 can be any type of antenna including patch antennas and dipole antennas.

Figure 2:
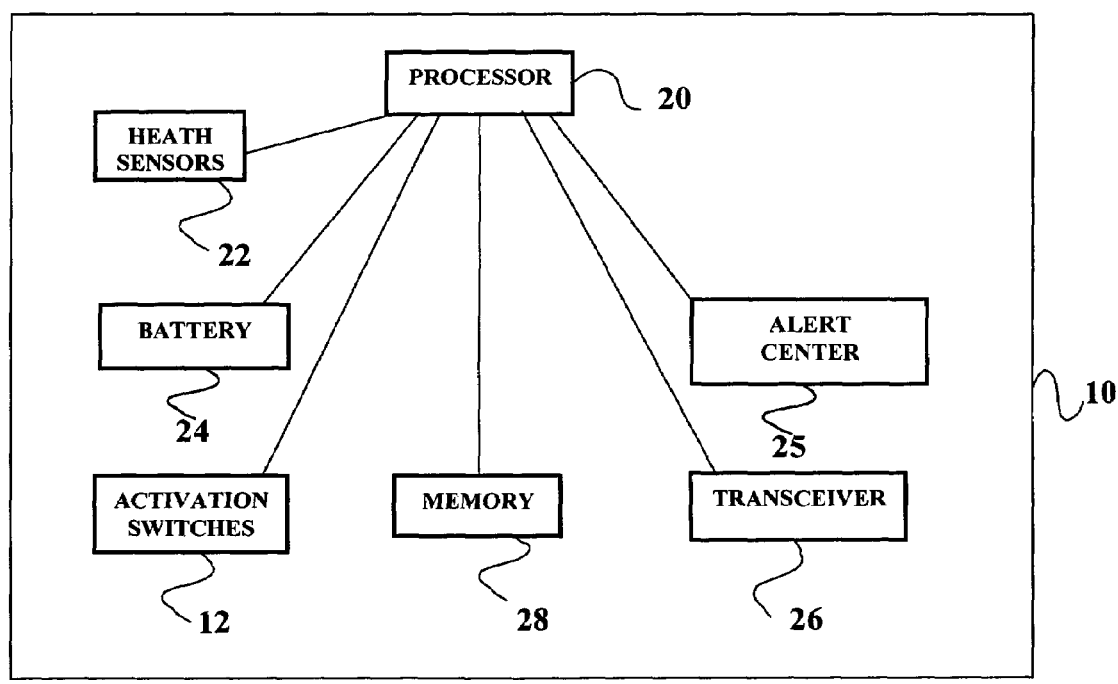
FIG. 2 is a block diagram of portable health monitoring system

Referring now to FIG. 2, in one embodiment, portable health monitoring system 10 comprises a processor 20 interconnected with switches 12, heath sensors 22, memory 28, transceiver 26, battery 24, and alert center 25.

Figure 3:
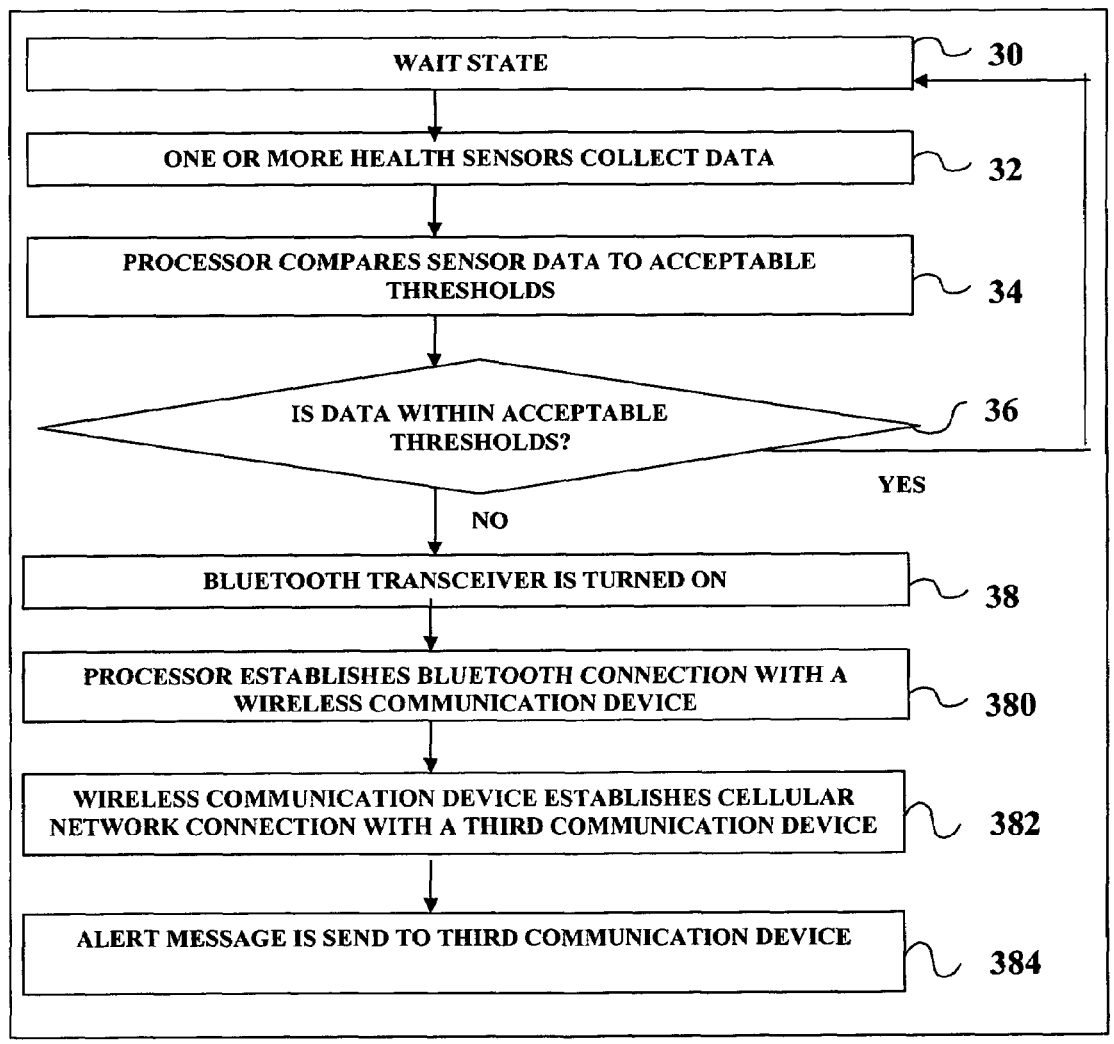
FIG. 3 is a flowchart illustrating the operation of a portable health monitoring system

Turning now to FIG. 3, the flowchart illustrates the steps involved in the operation of health monitoring system.

In step 30 the portable health monitoring system is in sleep mode. In step 32, health sensors 22 collect data. In step 34, processor 20 compares collected sensor data to acceptable threshold conditions. In step 36, if data is within acceptable thresholds, the system goes to a wait state in step 30 and sleeps for a period of time. If data is not within acceptable thresholds, transceiver 26 is turned on in step 38, and it establishes a wireless connection with a wireless communication device in step 380. Transceiver 26 can be a Bluetooth, WIFI, WiMax transceiver, or any widely available protocol based transceiver technology. In the case of Bluetooth, a Bluetooth transceiver (class 2) can discover any Bluetooth transceiver within a radius of 10 meters seamlessly. A class 1 Bluetooth transceiver can detect any Bluetooth transceiver within a radius of 100 meters.

Launched in 1994 by Ericsson, Bluetooth began as a project to unify communication between different types of electronic devices without the use of cumbersome cable connections. In fact, Bluetooth was taken from the nickname of Viking king, Harald II—who unified warring Viking tribes during the tenth century—and whose discolored teeth were a result of his partiality for blueberries and blackberries.

Bluetooth uses radio chips in electronic devices to enable connectivity over the 2.4 GHz radio frequency (RF) band. The Bluetooth specification (a de facto standard containing information required to ensure that devices supporting Bluetooth can communicate with each other worldwide) defines two transmission ranges for personal area networking. The range is between 10 m and 100 m without a line of sight requirement. The radio link is capable of voice and data transmission up to a maximum capacity of 720 kbps per channel.

In step 382, the wireless communication device dials and establishes a cellular network communication with at least a third communication device based on user parameters and user rules.

In a configuration step, the user defines what phone numbers to dial or SMS or what email addresses to email. The user also defines the rules and conditions under which those numbers/emails are dialed/emailed and what messages are sent. When those conditions occur, those phone numbers are emailed and those SMS/emails are sent.

A cellular network communication is any communication that initiates from a mobile telephony network. Third communication device can be a PSTN phone, a mobile phone, a cable phone, a WIFI phone, a VoIP phone or any telephone system.

In step 384, an alert message is sent to third communication device. The alert message may contain prerecord messages, data, data converted to voice through a synthesizer, or any combination of the above. Alert message may also be an email.

Figure 4:
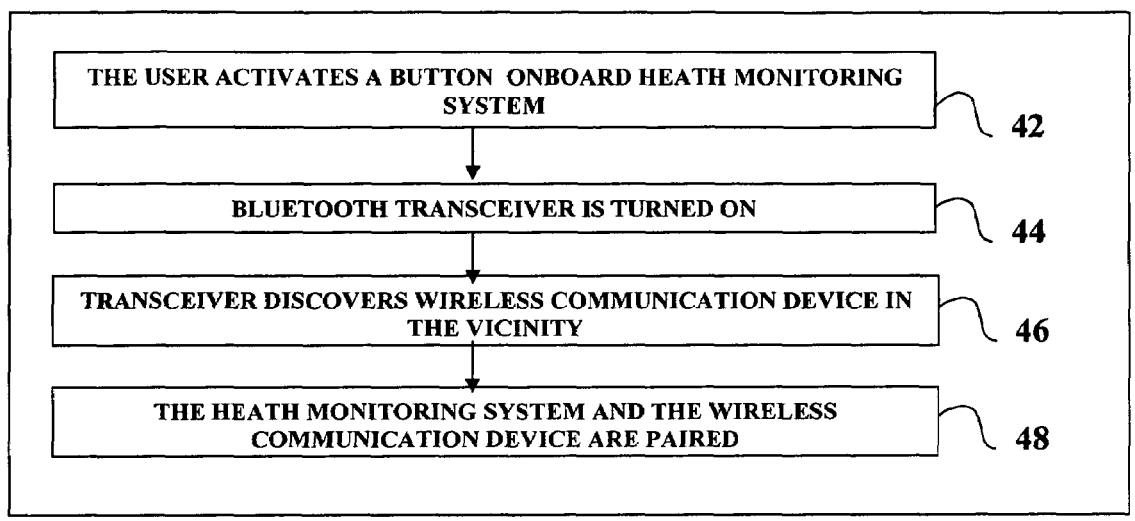
FIG. 4 is a flowchart illustrating initiating the portable health monitoring system

Turning now to FIG. 4, the flowchart illustrates the steps involved in initiating the portable health monitoring system.

In step 42, the user activates switch 12 and transceiver 26 is turned on in step 44. In step 46, it discovers a wireless communication device in the vicinity. An LED, a buzzer or an audio device may be activated to inform the user of the success/failure of the operation. In step 48, the devices are paired. The user may be prompted to authorize and authenticate the devices. Thus the devices will be paired.

Currently, products allow for a single pairing to be maintained and therefore, if a user moves from his or her car to the office, he or she needs to re-establish the pairing between the mobile phone and Bluetooth headset. Future Bluetooth chipsets are expected to store pairing information so that devices can reconnect automatically once the initial pairing has been set up.

A Bluetooth network is completely self organising, and ad hoc personal area networks (PANs) can be established wherever two or more Bluetooth devices are sufficiently close to establish radio contact. Equipment capable of Bluetooth connectivity is able to self-organise by automatically searching its vicinity for other Bluetooth-enabled devices. Upon establishing a contact, information is exchanged which determines if the connection should be completed or not.

During this first encounter, the Bluetooth devices connect via a process of authorisation and authentication.

Here is how Bluetooth devices connect to each other: Unlike the wired technology Bluetooth is designed to replace, a Bluetooth device does not have to be aware of the devices and capabilities they are attaching to. There is a built in mechanism to inquire for devices, connect to them and once connected discover the services they possess in their database. In its simplest form the devices needing to connect proceed as follows:

1) The master enters inquiry mode and sends out an inquiry to discover devices available to connect to.
2) Potential slaves make themselves discoverable by entering inquiry scan mode and listen for an inquiry from a master.
3) On receiving an inquiry, the slave responds to the master with a Frequency Hop Synchronization packet (FHS). The FHS contains information that is needed to create a connection to the device; this information includes its Bluetooth address and class of device.
4) The master collects the FHS information from each device discovered.
5) To connect to one of these devices the master goes into page mode and will page the device using the corresponding Bluetooth address.

Figure 5:
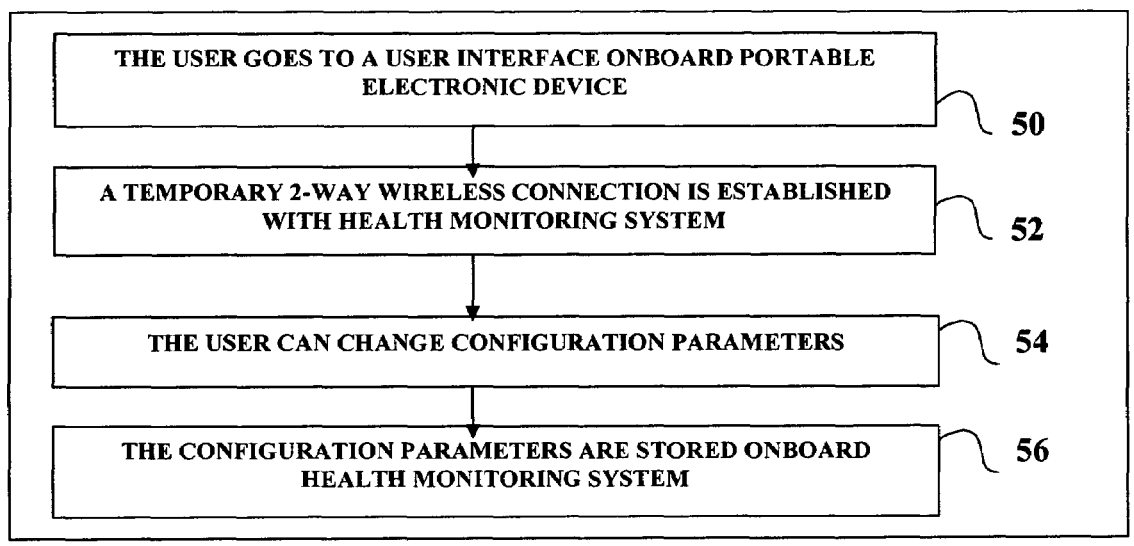
FIG. 5 is a flowchart illustrating configuring the portable health monitoring system Similar reference numerals are used in different figures to denote similar components.

The slave being paged by a master will need to be in page scan mode to be able to connect to a master Turning now to FIG. 5, the flowchart illustrates the steps involved in configuring the health monitoring system 10 using portable electronic device.

In step 50, the user launches a user interface onboard the portable electronic device. A two-way wireless connection is established with the health monitoring system in step 52. The user interface may display existing configuration parameters. The user interface allows the user to set configuration parameters or to change them in step 54. Configuration parameters may include data thresholds such as acceptable temperature, acceptable blood pressure, acceptable heart rate, acceptable insulin level, acceptable pulse, operation hours, operation days, alert messages, buzzer type, buzzer volume, buzzer duration, alarm type. The configuration parameters are stored onboard the health monitoring system in step 56.

The user interface is a program that can be installed onboard the portable electronic device from the monitoring device, from a CD, or from other medium such as Internet.

Numerous other modifications, variations, and adaptations may be made to the particular embodiment of the invention described above without departing from the scope of the invention, which is defined in the claims. Hence, while exemplary embodiments of the present invention have been set forth above, it is to be understood that the pioneer inventions disclosed herein may be constructed or used otherwise than as specifically described.

What is claimed is:

1. A unitary remotely configurable portable health monitoring system comprising:
   health sensor means for collecting data,
   Bluetooth transceiver means for establishing a two-way wireless connection with a second device in range,
   memory for storing one or more alert messages,
   one or more batteries,
   a processor for evaluating data from health sensor means and comparing it to acceptable ranges,
   if said data is outside said acceptable ranges,
   said processor reads output from said health sensor means and converts it to synthetic voice,
   said processor transmits phone numbers to said second device,
   said processor transmits instructions to said second device to dial a third device corresponding to said phone numbers,
   said processor transmits said alert messages and said synthetic voice when a first Bluetooth wireless connection has been established between said Bluetooth transceiver and said second device in range and a second cellular network connection has been established between said second device and said third device.

2. The device of claim 1 wherein said health sensor means is selected from the set comprised of an infrared detector, a temperature reader, a blood pressure reader, a heart rate reader, an insulin reader, a prosthesis data reader, a vibration detector, a colour detector, a pulse oximeter, a CO2 detector.

3. The device of claim 1 wherein said second device in range is a wireless communication device.

4. The device of claim 1 wherein said one or more batteries are rechargeable batteries.

5. The device of claim 1 comprising means for attaching said portable health monitoring system selected from the set containing: clip, ring, fastening mechanism.

6. A method for health monitoring using a unitary remotely configurable rule-based portable monitoring system comprising:
   reading data from health sensor means,
   comparing said data to acceptable thresholds,
   on detecting an exception,
      a transceiver is turned on,
      a short range two-way wireless connection is established with a second wireless communication device in range compatible with said transceiver,
      said second wireless communication device: dials one or more alert phone numbers, establishes cellular network communication with a third communication device,
      data from said health sensor means is converted to synthetic voice and transmitted to said third communication device.

7. The method of claim 6 whereby said second wireless communication device is selected from the set comprising a cellular phone, a personal digital assistant (PDA), a wireless email device, an instant messaging device, a pager.

8. The method of claim 6 wherein said health sensor means is selected from the set comprised of an infrared detector, a temperature reader, a blood pressure reader, a heart rate reader, an insulin reader, a prosthesis data reader, a vibration detector, a colour detector, a pulse oximeter, a CO2 detector.

9. The method of claim 6 wherein said transceiver is a Bluetooth transceiver.

10. The method of claim 6 wherein said transceiver is a WIFI transceiver.

11. The method of claim 6 comprising, starting a configuration application onboard said second wireless communication device, establishing a temporary two-way wireless connection with said portable monitoring system, sending configuration parameters to said portable monitoring system, said configuration parameters are stored onboard said portable monitoring system.

12. The method of claim 11 whereby said configuration parameters comprise parameters selected from the set containing: acceptable thresholds, operation hours, operation days, buzzer type, buzzer volume, buzzer duration, alarm type.

13. The method of claim 6 comprising, starting a configuration application onboard said second wireless communication device, establishing a temporary two-way wireless data connection with said portable monitoring system, sending a set of configuration parameters to said portable monitoring system, said set of configuration parameters are stored onboard said portable monitoring system.

14. The method of claim 13 comprising, setting a second set of configuration parameters, said second set of configuration parameters is stored onboard said wireless communication device.

* * * * *